(12) United States Patent
Chin et al.

(10) Patent No.: US 6,776,945 B2
(45) Date of Patent: Aug. 17, 2004

(54) MEDICAL DEVICE WITH EXTRUDED MEMBER HAVING HELICAL ORIENTATION

(75) Inventors: Albert Chin, Newton, MA (US); John Chen, Plymouth, MN (US); Lixiao Wang, Long Lake, MN (US); Ronald Sahatjian, Lexington, MA (US); (Bruce) Yiqun Wang, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 10 days.

(21) Appl. No.: 09/898,710

(22) Filed: Jul. 3, 2001

(65) Prior Publication Data

US 2003/0009114 A1 Jan. 9, 2003

(51) Int. Cl.[7] .............................................. B29C 47/20
(52) U.S. Cl. ............................... 264/171.26; 264/209.2
(58) Field of Search ....................... 264/171.26, 209.2, 264/209.3, 210.2; 600/585

(56) References Cited

U.S. PATENT DOCUMENTS

| | | | | |
|---|---|---|---|---|
| 2,616,126 A | * | 11/1952 | Merck et al. ............... 600/585 |
| 3,404,203 A | * | 10/1968 | Donald ..................... 264/209.2 |
| 3,891,374 A | * | 6/1975 | Ninomiya et al. .......... 264/569 |
| 4,293,294 A | | 10/1981 | Rasmussen |
| 4,447,239 A | | 5/1984 | Krütten |
| 4,657,024 A | | 4/1987 | Coneys |
| 4,790,970 A | * | 12/1988 | Kurth et al. ................ 264/130 |
| 4,990,143 A | | 2/1991 | Sheridan |
| 5,059,375 A | * | 10/1991 | Lindsay .................... 264/167 |
| 5,156,785 A | * | 10/1992 | Zdrahala ................... 264/209.2 |
| 5,248,305 A | * | 9/1993 | Zdrahala .................... 604/527 |
| 5,456,674 A | | 10/1995 | Bos et al. |
| 5,533,985 A | | 7/1996 | Wang |
| 5,622,665 A | | 4/1997 | Wang |
| 5,639,409 A | * | 6/1997 | van Muiden ............... 264/108 |
| 5,882,741 A | * | 3/1999 | Rubin et al. .............. 428/1.33 |
| 5,947,940 A | | 9/1999 | Beisel |
| 5,951,494 A | | 9/1999 | Wang et al. |
| 5,984,657 A | | 11/1999 | Bentivoglio |
| 6,436,056 B1 | * | 8/2002 | Wang et al. ................ 600/585 |

FOREIGN PATENT DOCUMENTS

| | | |
|---|---|---|
| DE | 196 51 904 A1 | 6/1998 |
| JP | 2001-309533 | 11/2001 |
| WO | WO 95/29051 | 11/1995 |

OTHER PUBLICATIONS

U.S. patent application Ser. No. 09/898,717, Wang, filed Jul. 3, 2001.

Lusignea, R., "Flexible Multilayer Packaging with Oriented LCP Barrier Layer," *TAPPI Proceedings*, (1998) pp. 889–899.

* cited by examiner

*Primary Examiner*—Mark Eashoo
(74) *Attorney, Agent, or Firm*—Crompton, Seager & Tufte, LLC

(57) ABSTRACT

An elongate polymer member having molecular helical orientation formed by rotation immediately after passing through the extrusion head. The elongate polymer member is rotated downstream of the extrusion head in the molten state prior to solidification in order to impart the molecular helical orientation. Rotating the polymer member in the molten state allows the helical orientation to be imparted at the molecular level, and allows for more rotations per lineal foot of extrusion.

11 Claims, 4 Drawing Sheets

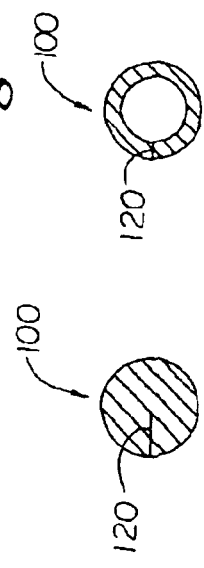
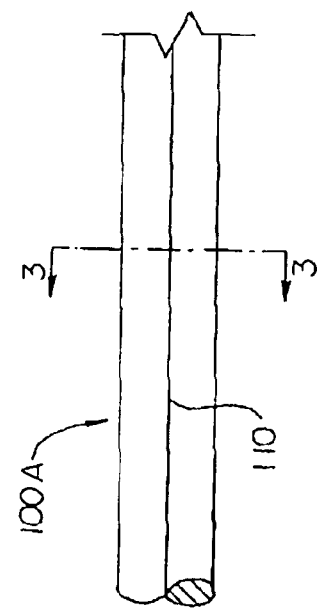
Fig. 3A  Fig. 3B
Fig. 2
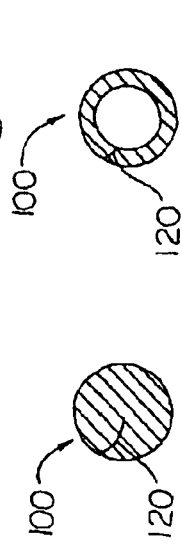
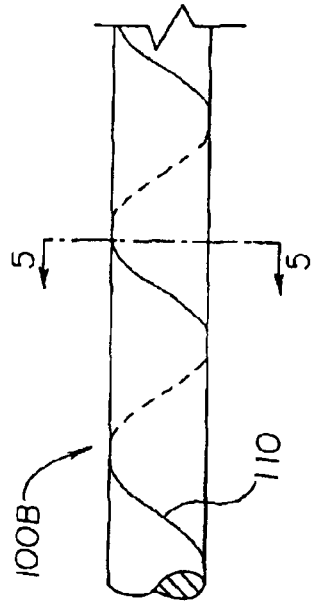
Fig. 5A  Fig. 5B
Fig. 4

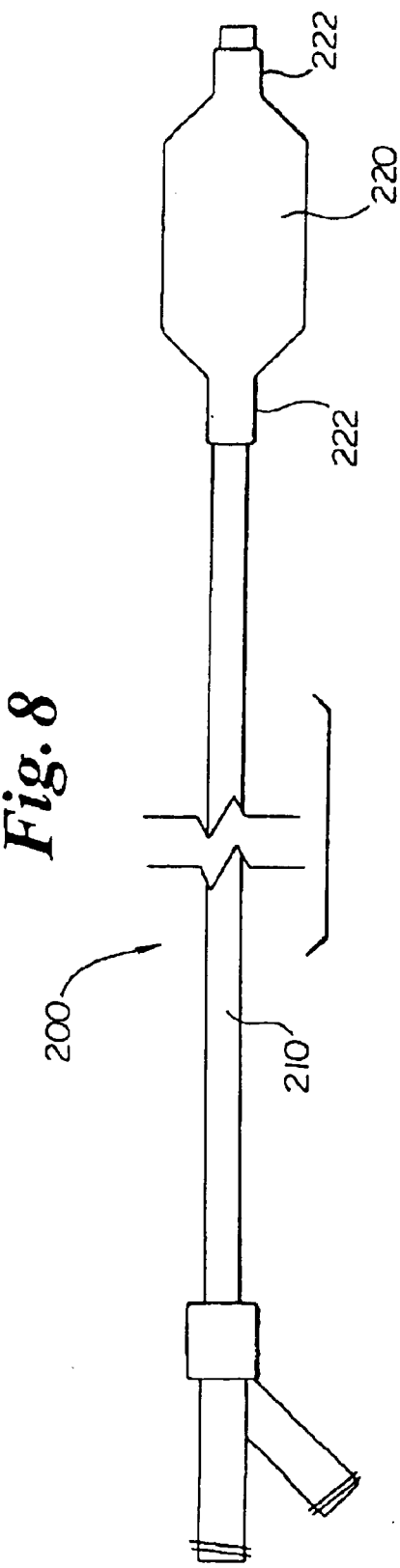
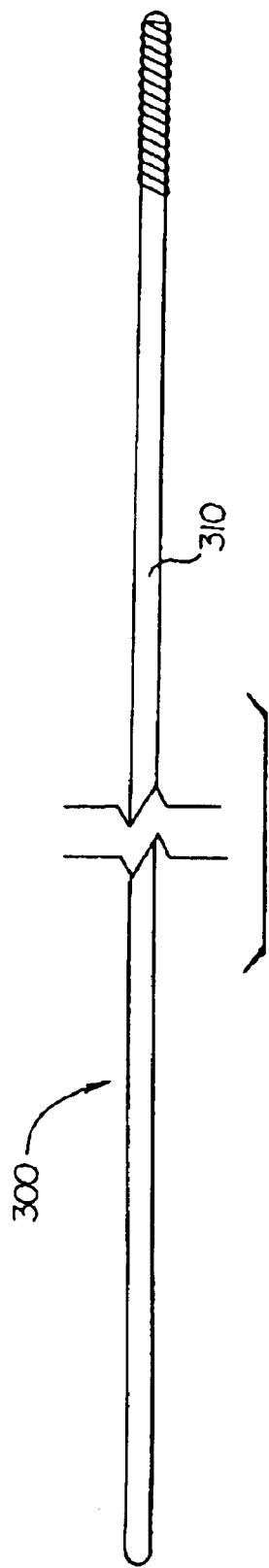

MEDICAL DEVICE WITH EXTRUDED MEMBER HAVING HELICAL ORIENTATION

FIELD OF THE INVENTION

The present invention generally relates to medical devices having extruded polymeric members. More specifically, the present invention relates to medical devices such as intravascular catheters and guide wires having extruded polymeric members with helical orientation.

BACKGROUND OF THE INVENTION

A wide variety of medical devices utilize extruded polymeric members. For example, intravascular catheters and guide wires commonly utilize an extruded polymeric member as a shaft component. Because intravascular catheters and guide wires must exhibit good torqueability, trackability and pushability, it is desirable that the extruded polymeric shaft component have good torque transmission, flexibility and column strength. These attributes are commonly incorporated into intravascular devices by utilizing a composite shaft construction. Alternatively, the polymer material which forms the shaft component may be oriented to enhance the mechanical characteristics thereof.

For example, U.S. Pat. No. 5,951,494 to Wang et al. discloses a variety of medical instruments, such as guide wires and catheters, formed at least in part of elongated polymer members having helical orientation. The helical orientation is established by processing an elongate polymer member with tension, heat and twisting. Wang et al. theorize that the tension, heat and twisting process results in a polymer member that has helical orientation on the molecular level. Such molecular helical orientation enhances torque transmission of the elongate polymer member, which is important for some types of intravascular medical devices that must be navigated through long and tortuous vascular pathways.

Wang et al. teach that the tension, heat and twisting is a post-processing technique performed on a preformed polymer member. The pre-formed polymer member may comprise, for example, a rod, a tube, a polymer-metal composite, or a polymer/non-metal composite. Because Wang et al. teach post-processing of a pre-formed polymer member, the resulting oriented polymer member inherently involves two (or more) separate processes. First, the polymer member must be formed by, for example, an extrusion process, and second, the polymer member must be oriented by post-processing (i.e., tension, heat and twisting).

Because these two separate processes may involve manufacturing inefficiencies, it is desirable to provide a single manufacturing process to form an elongate polymer member having helical molecular orientation. For example, it may be desirable to provide an extrusion process to obtain a polymer member with molecular helical orientation. However, to our present knowledge, such an extrusion process is not known in the prior art. Perhaps the closest examples of related extrusion processes are disclosed in U.S. Pat. No. 5,059,375 to Lindsay and U.S. Pat. No. 5,639,409 to Van Muiden.

Lindsay '375 discloses an extrusion process for producing flexible kink resistant tubing having one or more spirally-reinforced sections. The extruder includes a rotatable head having an extrusion passageway for spirally extruding a thermoplastic filament into a base thermoplastic material to form a spirally-reinforced tube. The rotatable head is rotated at a predetermined velocity to form the reinforcement filament in a spiral or helical pattern in the wall of the tubing. However, with this process, the wall of the tubing is not helically oriented at all, and neither the filament nor the wall of the tubing are helically oriented on the molecular level. Accordingly, the resulting tubing does not enjoy the advantages obtained by molecular helical orientation as disclosed in Wang et al.

Van Muiden '409 discloses an extrusion process for manufacturing a tube-like extrusion profile by conveying a number of divided streams of different polymeric materials to a rotating molding nozzle. The streams of material flow together in the rotating molding nozzle to form at least two helically shaped bands of material. After allowing the combined streams of material to cool off, an extrusion profile comprising a plurality of bands of polymeric material extending in a helical pattern is formed. However, the bands of material are not helically oriented on the molecular level as in Wang et al. since the helical pattern is imparted by the rotating nozzle when the polymeric materials are in a molten state.

From the foregoing, those skilled in the art will appreciate that there exists an unmet need for a single manufacturing process to form an elongate polymeric member having molecular helical orientation.

SUMMARY OF THE INVENTION

To address this unmet need, the present invention provides an elongate polymer member having molecular helical orientation formed by rotation immediately after passing through the extrusion head. In particular, the elongate polymer member is rotated downstream of the extrusion head in the molten state prior to solidification in order to impart the molecular helical orientation. The molten state refers to a state in which the polymer is below the melting temperature but above the glass transition temperature. Rotating the polymer member in the molten state allows the helical orientation to be imparted at the molecular level. In addition, rotating the polymer member in the molten state allows for more rotations per lineal foot than otherwise feasible with post-processing techniques.

The polymer member may be rotated at speeds of 1000 rpm or more, and preferably at 3,500 rpm or more. The extrusion rate may range from 10 fpm to 100 fpm, and preferably 20 fpm to 50 fpm. The resulting helical orientation ranges from 10 rotations per foot (rpf) to 350 rpf, and preferably ranges from 70 rpf to 175 rpf. The extrusion rate and/or the rotation rate may be varied during the extrusion process to vary the degree of molecular orientation at various positions along the elongate member.

The elongate polymer member may comprise a single polymer extrusion, a multi-polymer intermittent co-extrusion, or a multi-polymer continuous co-extrusion. The elongate polymer member may comprise a single layer, multiple layers, or a composite. The elongate polymer member may be extruded over a core member which may carry a substrate (e.g., PTFE tube, wire braid, wire coil, etc.) onto which the elongate polymer member is extruded. The core member may be removed after extrusion to form a tubular structure. The elongate polymer member may be fed back into the extrusion system for a second pass to create an outer layer preferably having a molecular helical orientation in the opposite direction from that of the first pass.

BRIEF DESCRIPTION OF THE DRAWINGS

FIG. 2 schematically illustrates an elongate polymer member without helical orientation;

FIG. 3A is a cross-sectional view taken along line 3—3 in FIG. 2 showing a solid polymer member;

FIG. 3B is a cross-sectional view taken along line 3—3 in FIG. 2 showing a tubular polymer member;

FIG. 4 schematically illustrates an elongate polymer member with molecular helical orientation;

FIG. 5A is a cross-sectional view taken along line 5—5 in FIG. 4 showing a solid polymer member;

FIG. 5B is a cross-sectional view taken along line 5—5 in FIG. 4 showing a tubular polymer member;

FIG. 8 illustrates an intravascular balloon catheter incorporating an extruded polymeric member having molecular helical orientation in accordance with the present invention; and FIG. 9 illustrates an intravascular guide wire incorporating an extruded polymeric member having molecular helical orientation in accordance with the present invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
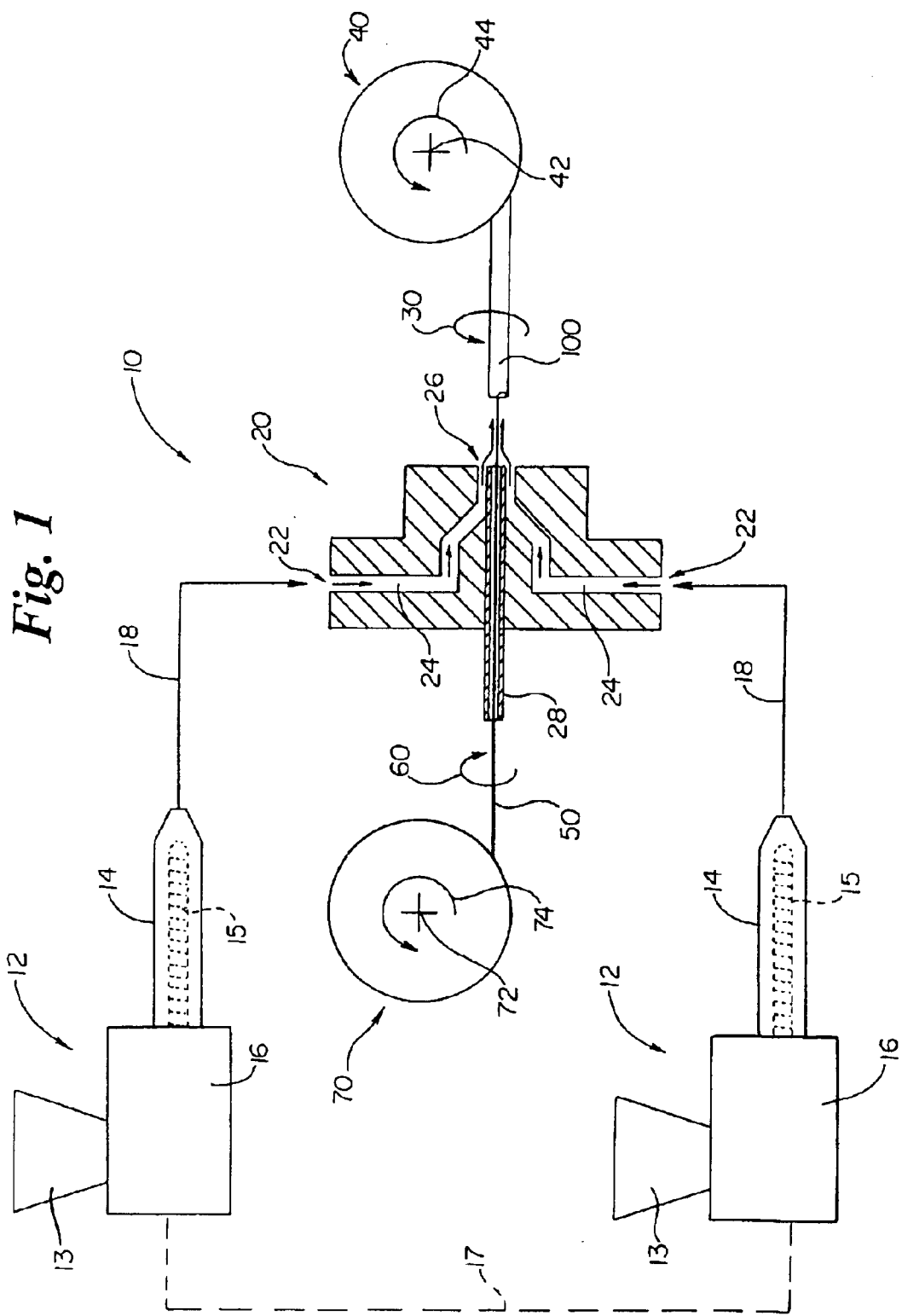
FIG. 1 is a schematic illustration of an extrusion system in accordance with an embodiment of the present invention, showing the extrusion head in cross section.

Refer now to FIG. 1 which illustrates an extrusion system 10 in accordance with the present invention. Extrusion system 10 includes one or more extruders 12 coupled to a non-rotatable extrusion head 20 as schematically illustrated by extrusion lines 18. Each extruder 12 includes a hopper 13, a heated barrel 14, an extrusion screw 15, and a control system 16, which may be coupled to other control systems of other extruders as indicated by dashed line 17 to facilitate co-extrusion.

Molten polymer enters the extrusion head 20 at inlets 22. The molten polymer flows through the extrusion passages 24 as indicated by the small arrows. The molten polymer exists the extrusion head 20 through outlet 26. Upon exiting the extrusion head 20 through outlet 26, the molten polymer begins to solidify thereby creating a molten polymer state. In the molten state, the polymer typically has a temperature below the melting point but at or above the glass transition point.

In this molten state, the elongate polymer member is rotated as indicated by arrow 30. The elongate polymer member 100 may be rotated manually or automatically by a suitable rotational drive mechanism. The direction of rotation 30 may be clockwise or counter clockwise as desired. By rotating the polymer member 100 in the molten state, a molecular helical orientation is imparted thereto. In particular, in the molten state, the crystalline regions of the polymer are helically oriented by rotation and subsequently allowed to cool to thereby lock-in the helical orientation. The molecular helical orientation imparted to the polymer member 100 is similar to the helical orientation imparted by the process disclosed in U.S. Pat. No. 5,951,494 to Wang et al., the entire disclosure of which is hereby incorporated by reference.

The elongate polymer member 100 may be cut into discrete lengths immediately after extrusion or spooled onto spool 40. Spool 40 rotates in a direction indicated by arrow 44 about an axis at the intersection of lines 42. If the elongate polymer member 100 is taken up by spool 40, the elongate polymer 100 and the spool 40 may be rotated simultaneously.

The elongate polymer member 100 may be formed by a single polymer or by multiple polymers by co-extrusion. For purposes of illustration only, the extrusion system 10 is shown as a two polymer co-extrusion system. Those skilled in the art will recognize that the extrusion head 20 and the number of extruders 12 may be modified depending on the number of polymers incorporated into the elongate polymer member 100.

The elongate polymer 100 may have a solid cross section or a tubular cross section. In addition, the elongate polymer member 100 may be extruded over a core member 50 which may be left in the elongate polymer member 100 or subsequently removed. The core member 50 is fed into the extrusion at 20 by guide tube 28. The core member 50 may comprise a metal wire or may comprise a composite substrate disposed on a metal wire. Examples of composite substrates include wire braid, wire coils, polymer braids, polymer coils, lubricious tubular members such as PTFE, etc. Subsequent to extrusion, the core member 50 may be removed to form a tubular elongate polymer member 100, with the substrate (if any) previously disposed on the core member 50 imbedded into the inside surface of the tubular elongate member 100.

If a core member 50 is used, the core member 50 is preferably rotated as indicated by arrow 60. Also preferably, the direction of rotation 60 of the core member 50 is the same as the direction of rotation 30 of the elongate polymer member 100. The core member 50 may be rotated manually or automatically by a suitable drive mechanism. The core member 50 may be disposed on spool 70 which rotates in the direction indicated by arrow 74 about an axis at the intersection of lines 72. If the core member 50 is provided on a spool 70, it may be necessary to rotate the spool 70 along with the core member 50 as indicated by arrow 60.

As an alternative, the core member 50 may comprise a previously formed polymer member 100 having helical orientation. In particular, the elongate polymer member 100 may be fed back into the extrusion system as a core member 50 for a second pass. The second pass creates an outer polymeric layer having a molecular helical orientation. Preferably, in the second pass, the elongate polymer member 100 and outer layer are rotated in the opposite direction from that of the first pass to provide helical orientation in different directions.

Refer now to FIGS. 2 and 4 which provide a schematic comparison between an elongate polymer member 100A without molecular helical orientation as shown in FIG. 2 and an elongate polymer member 100B with molecular helical orientation as shown in FIG. 4. The elongate polymer members 100A/100B are illustrated with longitudinal reference lines 110 and radial reference lines 120. Although reference lines 110/120 are visible on a macroscopic level, it can be appreciated by those skilled in the art that rotation of the polymer member 100 in the semi molten state results in molecular helical orientation only visible on the microscopic level. By comparison, it can be seen that rotation of the polymer member 100 in the molten state downstream of the extrusion head 20 results in a helical orientation of the reference lines 110/120. By the cross sectional views shown in FIGS. 4A and 4B, it can be appreciated that the helical orientation extends through the entire cross section of the polymer member 100B.

The polymer member 100 may be rotated at speeds of 1000 rpm or more, and preferably at 3,500 rpm or more. The extrusion rate may range from 10 fpm to 100 fpm, and preferably 20 fpm to 50 fpm. The resulting helical orientation ranges from 10 rotations per foot (rpf) to 350 rpf, and preferably ranges from 70 rpf to 175 rpf. The extrusion rate and/or the rotation rate may be varied during the extrusion process to vary the degree of molecular orientation at various positions along the elongate polymer member 100.

Figure 6:
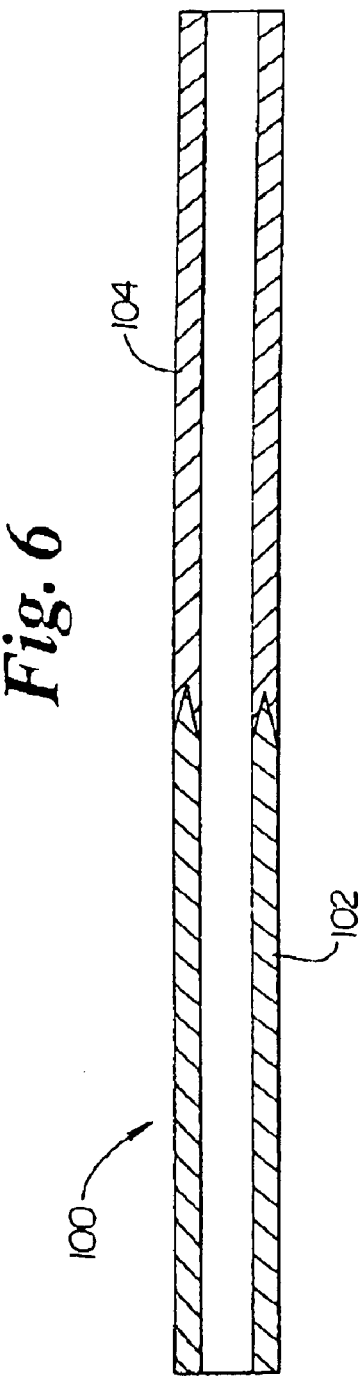
FIG. 6 schematically illustrates a longitudinal sectional view of an elongate polymer member having molecular helical orientation formed by intermittent co-extrusion.
Figure 7:
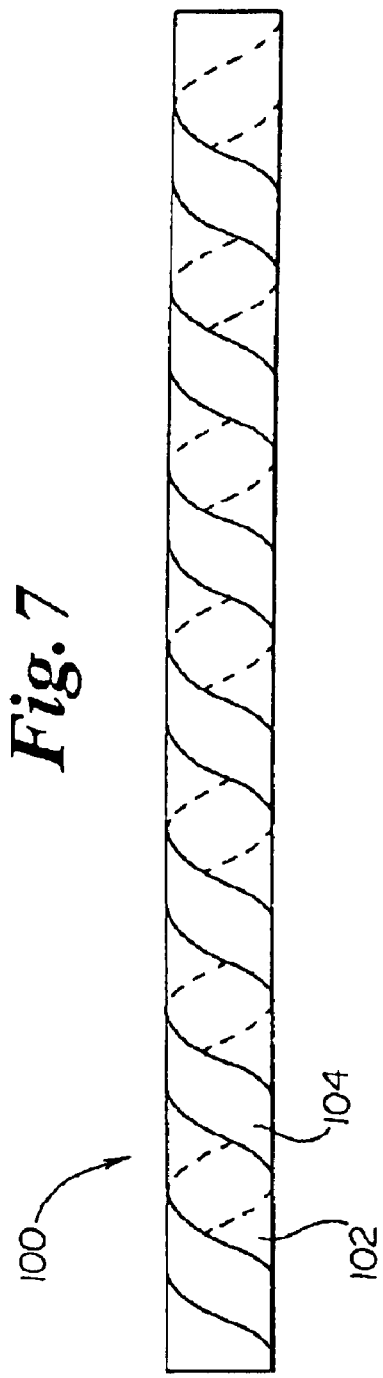
FIG. 7 schematically illustrates an elongate polymer member having molecular helical orientation formed by continuous co-extrusion.

As mentioned previously, the elongate polymer member 100 may comprise a single polymer extrusion or a multiple-polymer co-extrusion. FIG. 6 is a longitudinal sectional view of a polymeric tubular member 100 formed by intermittent co-extrusion. FIG. 7 is a plan view of a polymeric extrusion member 100 formed by continuous co-extrusion. As seen in FIG. 6, an intermittent co-extrusion process results in a polymeric extrusion member 100 comprising a first material 102 and a second material 104 disposed end-to-end, both of which have molecular helical orientation. With the exception of rotation downstream of the extrusion head, this type of co-extrusion is generally described in U.S. Pat. No. 5,533,985 to Wang, the entire disclosure of which is hereby incorporated by reference. As seen in FIG. 7, a continuous co-extrusion process results in a polymeric extrusion member 100 comprising a first polymeric material 102 and a second polymeric material 104 forming a helical band, both of which have molecular helical orientation. With the exception of rotation downstream of the extrusion head, this type of co-extrusion is generally described in U.S. Pat. No. 5,639,409 to Van Muiden, the entire disclosure of which is hereby incorporated by reference.

The polymeric extrusion member 100 may be incorporated into a wide variety of medical devices such as an intravascular catheter 200 illustrated in FIG. 8. Specifically, the elongate polymer member 100 having molecular helical orientation may be incorporated into the shaft 210 and/or the balloon 220 of the intravascular balloon catheter 200. In either case, the extruded polymeric member 100 may comprise a tubular member having one or more lumens extending therethrough. If incorporated into the inflatable balloon 220 of the intravascular balloon catheter 200, the polymeric tubular member 100 may comprise the balloon blank which is formed into the balloon 220 by a conventional blow-molding process. By incorporating the polymeric extrusion 100 into a catheter shaft 210, the molecular helical orientation improves kink-resistance and also allows for variable stiffness. By utilizing the polymeric member 100 to form the balloon 220, the molecular helical orientation provides better puncture resistance and higher burst strength, and may also be used to alter the compliance of the balloon 220. By utilizing the polymeric member 100 to form the balloon sleeve 222, the molecular helical orientation provides more flexibility such that the sleeve portion 222 behaves similar to the shaft 210, which is particularly beneficial if relatively stiff balloon materials are used to obtain the desired balloon performance.

By way of example, a catheter shaft 210 was made from a single-layered polymeric tube 100 formed from polyether block amide (PEBAX 7233 SA01) having 30% LCP (LKX1111) mixed therein. The tubing 100 was extruded and rotated at 3500 rpm in accordance with the present invention to have an inside diameter of 0.018 inches and an outside diameter 0.023 inches. The resulting shaft 210 exhibited better kink resistance than that formed without helical orientation. In addition, the helical orientation reduces the brittleness of shaft 210, particularly when high content LCP is used.

Also by way of example, a balloon 220 was made from a multi-layered polymeric tube 100 having seven layers. The first, third, fifth and seventh layers were formed from polyether block amide (PEBAX 7233 SA01), and the second, fourth and sixth layers were formed from polyether block amide (PEBAX 7233 SA01) having 10% LCP (LKX1111) mixed therein. The tubing 100 was extruded and rotated at 3500 rpm in accordance with the present invention to have an inside diameter of 0.0175 inches and an outside diameter of 0.0345 inches. The extruded tubing 100 was blow-molded to form a balloon 220 having an outside diameter of 3.0 mm, a length of 20 mm, and a wall thickness of 0.007 inches. The balloon 220 was tested to have a burst strength of 27198 psi at a burst pressure of 309 psi.

The polymeric extrusion member 100 may also be incorporated into an intravascular guide wire 300 illustrated in FIG. 9. The elongate tubular member 100 may comprise a solid cross section to form the shaft 310 or a tubular cross section to be disposed about a metallic core member of the shaft 310. By incorporating the polymeric extrusion 100 into a guide wire shaft 310, the molecular helical orientation improves kink-resistance and torque transmission, and also allows for variable stiffness.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of polymer extrusion, comprising the steps of:

providing an extruder having an extrusion head;
extruding an elongate polymer member;
solidifying the elongate polymer member wherein the elongate polymer member is formed of a polymer having a melt temperature and a glass transition temperature; and
rotating the elongate polymer member downstream of the extrusion head while the polymer is between the polymer melt temperature and the polymer glass transition temperature in order to impart molecular helical orientation to the elongate polymer member, without allowing the polymer temperature to drop below the polymer glass transition temperature and the step of rotating the polymer member downstream of the extrusion head is performed in close proximity to the extrusion head such that the molecular helical orientation is imparted to the elongate polymer member while the polymer is between the polymer melt temperature and the polymer glass transition temperature, without heating the elongate polymer member between the extruding step and rotating step, wherein the elongate polymer member is extruded at 10 fpm or more and rotated at 1000 rpm or more.

2. A method of polymer extrusion as in claim 1, wherein the elongate polymer member is rotated at 3500 rpm or more.

3. A method of polymer extrusion as in claim 1, wherein the elongate polymer member is rotated at a variable speed to vary the molecular helical orientation imparted to the elongate polymer member.

4. A method of polymer extrusion as in claim 1, wherein the step of extruding the elongate polymer member comprises co-extruding two or more polymers.

5. A method of polymer extrusion as in claim 1, wherein the elongate polymer member is extruded over a core member.

6. A method of polymer extrusion, comprising the steps of:
providing an extruder having an extrusion head;
extruding an elongate polymer member, wherein the step of extruding the elongate polymer member comprises co-extruding two or more polymers;
solidifying the elongate polymer member wherein the elongate polymer member is formed of a polymer having a melt temperature and a glass transition temperature; and
rotating the elongate polymer member downstream of the extrusion head while the polymer is between the polymer melt temperature and the polymer glass transition temperature in order to impart molecular helical orientation to the elongate polymer member, without allowing the polymer temperature to drop below the polymer glass transition temperature and the step of rotating the polymer member downstream of the extrusion head is performed in close proximity to the extrusion head such that the molecular helical orientation is imparted to the elongate polymer member while the polymer is between the polymer melt temperature and the polymer glass transition temperature, without heating the elongate polymer member between the extruding step and rotating step, wherein the step of co-extruding two or more polymers comprises intermittently co-extruding two or more polymers.

7. A method of polymer extrusion as in claim 4, wherein the step of co-extruding two or more polymers comprises continuously co-extruding two or more polymers.

8. A method of polymer extrusion as in claim 5, wherein the core member is rotated with the elongate polymer member.

9. A method of polymer extrusion as in claim 8, wherein the core member is removed from the polymer member.

10. A method of polymer extrusion, comprising the steps of:
providing an extruder having an extrusion head;
extruding an elongate polymer member;
solidifying the elongate polymer member wherein the elongate polymer member is formed of a polymer having a melt temperature and a glass transition temperature;
rotating the elongate polymer member downstream of the extrusion head while the polymer is between the polymer melt temperature and the polymer glass transition temperature in order to impart molecular helical orientation to the elongate polymer member, without allowing the polymer temperature to drop below the polymer glass transition temperature and the step of rotating the polymer member downstream of the extrusion head is performed in close proximity to the extrusion head such that the molecular helical orientation is imparted to the elongate polymer member while the polymer is between the polymer melt temperature and the polymer glass transition temperature, without heating the elongate polymer member between the extruding step and rotating step;
feeding the elongate polymer member back into the extruder as a core member;
extruding a second elongate polymer member over the core member;
solidifying the second elongate polymer member; and
rotating the second elongate polymer member downstream of the extrusion head while the polymer is between the polymer melt temperature and the polymer glass transition temperature in order to impart molecular helical orientation to the second elongate polymer member.

11. A method of polymer extrusion as in claim 10, wherein the second polymer member is rotated in a different direction than the first polymer member.

* * * * *